United States Patent [19]

Camden

[11] Patent Number: 5,665,751

[45] Date of Patent: Sep. 9, 1997

[54] PHARMACEUTICAL COMPOSITION FOR INHIBITING THE GROWTH OF CANCERS

[75] Inventor: James Berger Camden, West Chester, Ohio

[73] Assignee: The Procter & Gamble Company, Cincinnati, Ohio

[21] Appl. No.: 473,818

[22] Filed: Jun. 7, 1995

[51] Int. Cl.⁶ ............................................. A61K 31/425
[52] U.S. Cl. ........................................................ 514/383
[58] Field of Search ............................................. 514/385

[56] References Cited

U.S. PATENT DOCUMENTS

| | | | |
|---|---|---|---|
| 4,079,062 | 3/1978 | Van Reet et al. | 260/8 |
| 4,160,838 | 7/1979 | Van Reet et al. | 424/269 |
| 4,404,216 | 9/1983 | Richardson | 514/383 |
| 5,126,359 | 6/1992 | Stroech et al. | 514/383 |
| 5,360,612 | 11/1994 | Fries et al. | 514/383 |

FOREIGN PATENT DOCUMENTS

| | | |
|---|---|---|
| 1004029 | 9/1992 | Belgium . |
| 44605 | 1/1982 | European Pat. Off. . |
| 2078719 | 1/1982 | United Kingdom . |

OTHER PUBLICATIONS

Copending Application of Camden, serial No. 08/674,182, filed Jul. 16, 1996 claiming priority to provisional application, serial No. 60/001,838 and copending application 08/473,819, filed Jun. 7, 1995.
Benzaquen, et al. Nature Medicine, 1,(6) Jun. 1995.
Physician's Desk Reference, 15:35:33, Medical Economics Data Production Company, Montvale, NJ, 1995.
Schwartz, et al., "Inhibition of all–trans–retinoic acid Metabolism by Fluconazole in vitro and in Patients with Acute Promyelocytic Leukemia" Biochem Pharmacol., vol. 50, No. 7, pp. 923–928 (Sep., 1995).
Copending Application of J. B. Camden, Ser. No. 08/674,180; filed Jul. 16, 1996.
Copending Application of J. B. Camden, Ser. No. 08/473,819; filed Jun. 7, 1995.

*Primary Examiner*—James H. Reamer
*Attorney, Agent, or Firm*—R. A. Dabek; J. C. Rasser

[57] ABSTRACT

A pharmaceutical composition that inhibits the growth of tumors and cancers in mammals comprising fungicide is disclosed. The particular fungicide used is a 1,3-bis-triazolyl-2-propanol derivative. These compositions are also effective against viral infections.

16 Claims, No Drawings

PHARMACEUTICAL COMPOSITION FOR INHIBITING THE GROWTH OF CANCERS

TECHNICAL FIELD

This invention is a pharmaceutical composition that inhibits the growth of cancers and tumors in mammals, particularly in human and warm blooded animals. The composition contains a 1,3-bis-triazolyl-2-propanol derivative.

BACKGROUND OF THE INVENTION

Cancers are the leading cause of death in animals and humans. The exact cause of cancer is not known, but links between certain activities such as smoking or exposure to carcinogens and the incidence of certain types of cancers and tumors has been shown by a number of researchers.

Many types of chemotherapeutic agents have been shown to be effective against cancers and tumor cells, but not all types of cancers and tumors respond to these agents. Unfortunately, many of these agents also destroy normal cells. The exact mechanism for the action of these chemotherapeutic agents are not always known.

Despite advances in the field of cancer treatment the leading therapies to date are surgery, radiation and chemotherapy. Chemotherapeutic approaches are said to fight cancers that are metastasized or ones that are particularly aggressive. Such cytocidal or cytostatic agents work best on cancers with large growth factors, i.e., ones whose cells are rapidly dividing. To date, hormones, in particular estrogen, progesterone and testosterone, and some antibiotics produced by a variety of microbes, alkylating agents, and anti-metabolites form the bulk of therapies available to oncologists. Ideally cytotoxic agents that have specificity for cancer and tumor cells while not affecting normal cells would be extremely desirable. Unfortunately, none have been found and instead agents which target especially rapidly dividing cells (both tumor and normal) have been used.

Clearly, the development of materials that would target tumor cells due to some unique specificity for them would be a breakthrough. Alternatively, materials that were cytotoxic to tumor cells while exerting mild effects on normal cells would be desirable. Therefore, it is an object of this invention to provide a pharmaceutical composition that is effective in inhibiting the growth of tumors and cancers in mammals with mild or no effects on normal cells.

More specifically, it is an object of this invention to provide an anti-cancer composition comprising a pharmaceutical carrier and a 1,3-bis-triazolyl-2-propanol derivative as defined herein along with a method for treating such cancers.

These and other objects will become evident from the following detailed description of this inventions.

SUMMARY OF THE INVENTION

A pharmaceutical composition for treatment of mammals, and in particular, warm blooded animals and humans, comprising a pharmaceutical carrier and an effective amount anti-cancer compound selected from the group consisting of:

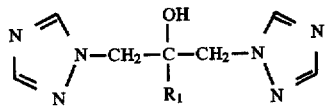

wherein $R^1$ is an optionally substituted alkyl, cycloalkyl (e.g. cyclopentyl or cyclohexyl), aryl or haloaryl (e.g. phenyl or 2,4-dichlorophenyl) or aralkyl (e.g., benzyl); and salts and metal complexes and ethers or esters thereof, and the non-toxic, pharmaceutically acceptable acid addition salts with both organic and inorganic acids. Specifically, such his triazole derivatives as 2-(2,4-dichlorophenyl)-1,3-bis(1H-1, 2,4-triazole-1-yl)propan-2-ol and its corresponding 2- and 4-chlorophenyl analogs and 2,4-diflourophenyl analogs are claimed.

These compositions can be used to inhibit the growth of cancers, leukemia and other tumors in humans or animals by administration of an effective amount either orally, rectally, topically or parenterally, intravenously or by injection into the tumor. These compositions do not significantly affect healthy cells as compared to adriamycin which has a detrimental effect on healthy cells.

These compositions are also effective against viruses. Therefore it is an object of this invention to provide a composition effective against HIV, herpes, influenza, rhinoviruses and the like.

DETAILED DESCRIPTION OF THE INVENTION

A. Definitions

As used herein, the term "comprising" means various components can be conjointly employed in the pharmaceutical composition of this invention. Accordingly, the terms "consisting essentially of" and "consisting of" are embodied in the term comprising.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutical addition salts" is salt of the anti-cancer compound with an organic or inorganic acid. These preferred acid addition salts are chlorides, bromides, sulfates, nitrates, phosphates, sulfonates, formates, tartrates, maleates, malates, citrates, benzoates, salicylates, ascorbates, and the like.

As used herein, a "pharmaceutical carrier" is a pharmaceutically acceptable solvent, suspending agent or vehicle for delivering the anti-cancer agent to the animal or human. The carrier may be liquid or solid and is selected with the planned manner of administration in mind.

As used herein, "cancer" refers to all types of cancers or neoplasm or malignant tumors, including leukemia, found in mammals.

As used herein, the "anti-cancer compounds" are the 1,3-bis-triazolyl-2-propanols, and their salts. The exact 1,3-bis-triazolyl-2-propanols are described in detail below. The preferred materials are the products sold under the names "fluconazole®" by Pfizer.

As used herein, "viruses" includes viruses which cause diseases (vital infection) in man and other warm blooded animals such as HIV virus, herpes, influenza and rhinoviruses.

B. THE ANTI-CANCER COMPONDS

The anti-cancer compounds are 1,3-bis-triazolyl-2-propanol derivatives which are known for their antifungal activities. They are systemic fungicides used to prevent and eradicate fungi. The compounds have the following structure:

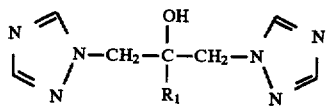

wherein $R^1$ is an optionally substituted alkyl, cycloalkyl (e.g. cyclopentyl or cyclohexyl), aryl or haloaryl (e.g. phenyl or 2,4-dichlorophenyl) or aralkyl (e.g., benzyl); and salts and metal complexes and ethers or esters thereof, and the non-toxic, pharmaceutically acceptable acid addition salts with both organic and inorganic acids. Specifically, such bis triazole derivatives as 2-(2,4-dichloropheyl)-1,3-bis(1H-1,2,4-triazole-1-yl)propan-2-ol and its corresponding 2- and 4-chlorophenyl analogs and 2,4-diflourophenyl analogs are useful herein. Preferably the composition is 2-(2,4-difluorophenyl)1,3-bis(1H-1,2,4-triazol-1-yl)propan-2-ol and its pharmaceutically acceptable acid addition salts with both organic and inorganic acids.

These compounds are prepared according to the method described in U.S. Pat. No. 4,404,216 issued to Richardson, Sep. 13, 1983 and British Patent Application No. 2,078,719A published Jan. 13, 1982 and European patent application No. 44,605 published Jan. 27, 1982 (both assigned to Imperial Chemical Industries Ltd).

It is believed that these particular fungicides have the capability of reducing tumors or decreasing their growth significantly because of their ability to inhibit the synthesis of sterols.

C. DOSAGE

Any suitable dosage may be given in the method of the invention. The type of compound and the carrier and the amount will vary widely depending on the species of the warm blooded animal or human, body weight, and tumor, virus, cancer or disease being treated. Generally a dosage of between about 2 milligrams (mg) per kilogram (kg) of body weight and about 400 mg per kg of body weight is suitable. Preferably from 15 mg to about 150 mg/kg of body weight is used. Generally, the dosage in man is lower than for small warm blooded mammals such as mice. A dosage unit may comprise a single compound or mixtures thereof with other compounds or other cancer inhibiting compounds. The dosage unit can also comprise diluents, extenders, carriers and the like. The unit may be in solid or gel form such as pills, tablets, capsules and the like or in liquid form suitable for oral, rectal, topical, intravenous injection or parenteral administration or injection into or around the tumor.

D. DOSAGE DELIVERY FORMS

The anti-cancer compounds are typically mixed with a pharmaceutically acceptable carrier. This carrier can be a solid or liquid and the type is generally chosen based on the type of administration being used. The active agent can be coadministered in the form of a tablet or capsule, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms would also include minerals and other materials to make them compatible with the type of injection or delivery system chosen.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described in the following references: 7 Modem Pharmaceutics, Chapters 9 and 10 (Banker & Rhodes, Editors, 1979); Lieberman et at., Pharmaceutical Dosage Forms: Tablets (1981); and Ansel, Introduction to Pharmaceutical Dosage Forms 2nd Edition (1976).

E. METHOD OF TREATMENT

The method of treatment can be any suitable method which is effective in the treatment of the particular cancer or tumor type or virus that is being treated. Treatment may be oral, rectal, topical, parenteral or intravenous administration or by injection into the tumor and the like. The method of applying an effective amount also varies depending on the tumor being treated. It is believed that parenteral treatment by intravenous, subcutaneous, or intramuscular application of the 1,3-bis-triazolyl-2-propanol compounds, formulated with an appropriate carrier, additional cancer inhibiting compound or compounds or diluent to facilitate application will be the preferred method of administering the compounds to warm blooded animals.

What is claimed is:

1. A method of treating cancer and viral infections in warm blooded mammals comprising administering a safe and effective amount of a 1,3-bis-triazolyl-2-propanol derivative of the formula:

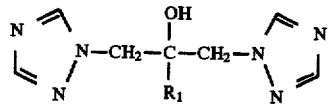

wherein $R^1$ is a substituted alkyl, cycloalkyl, aryl or haloaryl or aralkyl; and salts and metal complexes and ethers or esters thereof, and the non-toxic, pharmaceutically acceptable acid addition salts with both organic and inorganic acids.

2. A method according to claim 1 wherein from about 2 mg/kg body weight to about 400 mg/kg of said 1,3-bis-triazolyl-2-propanol is administered.

3. A method according to claim 2 wherein said 1,3-bis-triazolyl-2-propanol is administered orally or enterically, intravenously, parenterally, parenterally or by injection into the tumor.

4. A method according to claim 3 wherein said 1,3-bis-triazolyl-2-propanol is administered in a solid form.

5. A method according to claim 4 wherein said solid form includes a carrier selected from the group consisting of lactose, sucrose, gelatin and agar.

6. A method according to claim 5 wherein from about 15 mg/kg to about 150 mg/kg of said 1,3-bis-triazolyl-2-propanol is administered.

7. A method according to claim 6 wherein said 1,3-bis-triazolyl-2-propanol is administered in a liquid form.

8. A method according to claim 7 wherein said liquid dosage from is selected from the group consisting of aqueous solutions, alcohol solutions, emulsions, suspensions, and suspensions reconstituted from non-effervescent and effervescent preparations and suspensions in pharmaceutically acceptable fats or oils.

9. A method according to claim 8 wherein said liquid dosage from a member selected from the group consisting of suspending agents, diluents, sweeteners, flavorants, colorants, preservatives, emulsifying agents and coloring agents, and mixtures thereof.

10. A method according to claim 3 wherein said 1,3-bis-triazolyl-2-propanol is selected from the group consisting of 2-(2,4-dichloropheyl)-1,3-bis(1H-1,2,4-triazole-1-yl)propan-2-ol and its corresponding 2- and 4- chlorophenyl analogs and 2,4-diflourophenyl analogs.

11. A method according to claim 10 wherein said pharmaceutically acceptable acid addition salts are selected from the group consisting of chlorides, bromides, sulfates, nitrates, phosphates, sulfonates, formates, tartrates, maleates, malates, citrates, benzoates, salicylates, ascorbates and mixtures thereof.

12. A method of treating influenza infections in warm blooded mammals comprising administering a safe and effective amount of a 1,3-bis-triazolyl-2-propanol derivative of the formula:

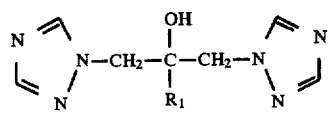

wherein $R^1$ is aryl or haloaryl or aralkyl and salts or metal complexes or ethers or esters thereof, and the non-toxic, pharmaceutically acceptable acid addition salts with organic or inorganic acids.

13. A method according to claim 12 wherein from about 2 mg/kg body weight to about 400 mg/kg is administered and wherein said 1,3-bis-triazolyl-2-propanol is α-(2,4-difluorophenyl)-α-(1H-1,2,4-triazol-1-ylmethyl)-1H-1,2,4-triazole-1-ethanol.

14. A method according to claim 13 wherein said 1,3-bis-triazolyl-2-propanol is administered orally, enterically, intravenously, or parenterally.

15. A method according to claim 13 wherein said 1,3-bis-triazolyl-2-propanol is administered in a solid form along with a pharmaceutically acceptable carrier.

16. A method according to claim 13 wherein said 1,3-bis-triazolyl-2-propanol is administered in a liquid form selected from the group consisting of aqueous solutions, alcohol solutions, emulsions, suspensions, and suspensions reconstituted from non-effervescent and effervescent preparations and suspensions in pharmaceutically acceptable fats or oils.

* * * * *